United States Patent
Gliner et al.

(10) Patent No.: US 11,759,252 B2
(45) Date of Patent: *Sep. 19, 2023

(54) MEDICAL INSTRUMENT WITH COAGULATION

(71) Applicant: Biosense Webster (Israel) Ltd., Yokneam (IL)

(72) Inventors: Vadim Gliner, Haifa (IL); Alon Boumendil, Giv''at Nili (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 38 days.

This patent is subject to a terminal disclaimer.

(21) Appl. No.: 17/580,730

(22) Filed: Jan. 21, 2022

(65) Prior Publication Data
US 2022/0202479 A1 Jun. 30, 2022

Related U.S. Application Data

(63) Continuation of application No. 16/375,198, filed on Apr. 4, 2019, now Pat. No. 11,272,980.

(51) Int. Cl.
| | |
|---|---|
| *A61B 18/14* | (2006.01) |
| *A61B 34/20* | (2016.01) |
| *A61B 34/30* | (2016.01) |
| *A61B 18/00* | (2006.01) |
| *A61B 18/12* | (2006.01) |

(52) U.S. Cl.
CPC ........ *A61B 18/1485* (2013.01); *A61B 34/20* (2016.02); *A61B 2018/00107* (2013.01); *A61B 2018/00327* (2013.01); *A61B 2018/00446* (2013.01); *A61B 2018/00589* (2013.01); *A61B 2018/00607* (2013.01); *A61B 2018/1266* (2013.01); *A61B 2034/2063* (2016.02); *A61B 2034/303* (2016.02)

(58) Field of Classification Search
CPC .......... A61B 18/1485; A61B 2018/303; A61B 2018/00327; A61B 2018/00607; A61B 34/20; A61B 2018/00589; A61B 18/1206; A61B 2018/00107; A61B 2034/303
See application file for complete search history.

(56) References Cited

U.S. PATENT DOCUMENTS

| | | | | |
|---|---|---|---|---|
| 5,795,298 | A  * | 8/1998 | Vesely | A61B 5/06 600/374 |
| 11,272,980 | B2 * | 3/2022 | Gliner | A61B 18/1442 |
| 2008/0300487 | A1 * | 12/2008 | Govari | A61B 34/20 600/443 |

* cited by examiner

*Primary Examiner* — Ronald Hupczey, Jr.
*Assistant Examiner* — Bradford C. Blaise
(74) *Attorney, Agent, or Firm* — Frost Brown Todd LLP

(57) ABSTRACT

In one embodiment, a medical system includes a medical instrument includes an elongated shaft having a distal end, at least one cutting element disposed at a distal end of the shaft, a position-tracking transducer disposed at the distal end of the shaft, and electrically insulated from the shaft and the at least one cutting element, and at least one metal coagulation electrode disposed at least partially over the position-tracking transducer, which electrically isolates the at least one metal coagulation electrode from the shaft, a signal generator coupled to apply an electrical current to the at least one metal coagulation electrode, and processing circuitry configured to receive signals generated by the position-tracking transducer, and track a location of the distal end responsively to the received signals.

20 Claims, 9 Drawing Sheets

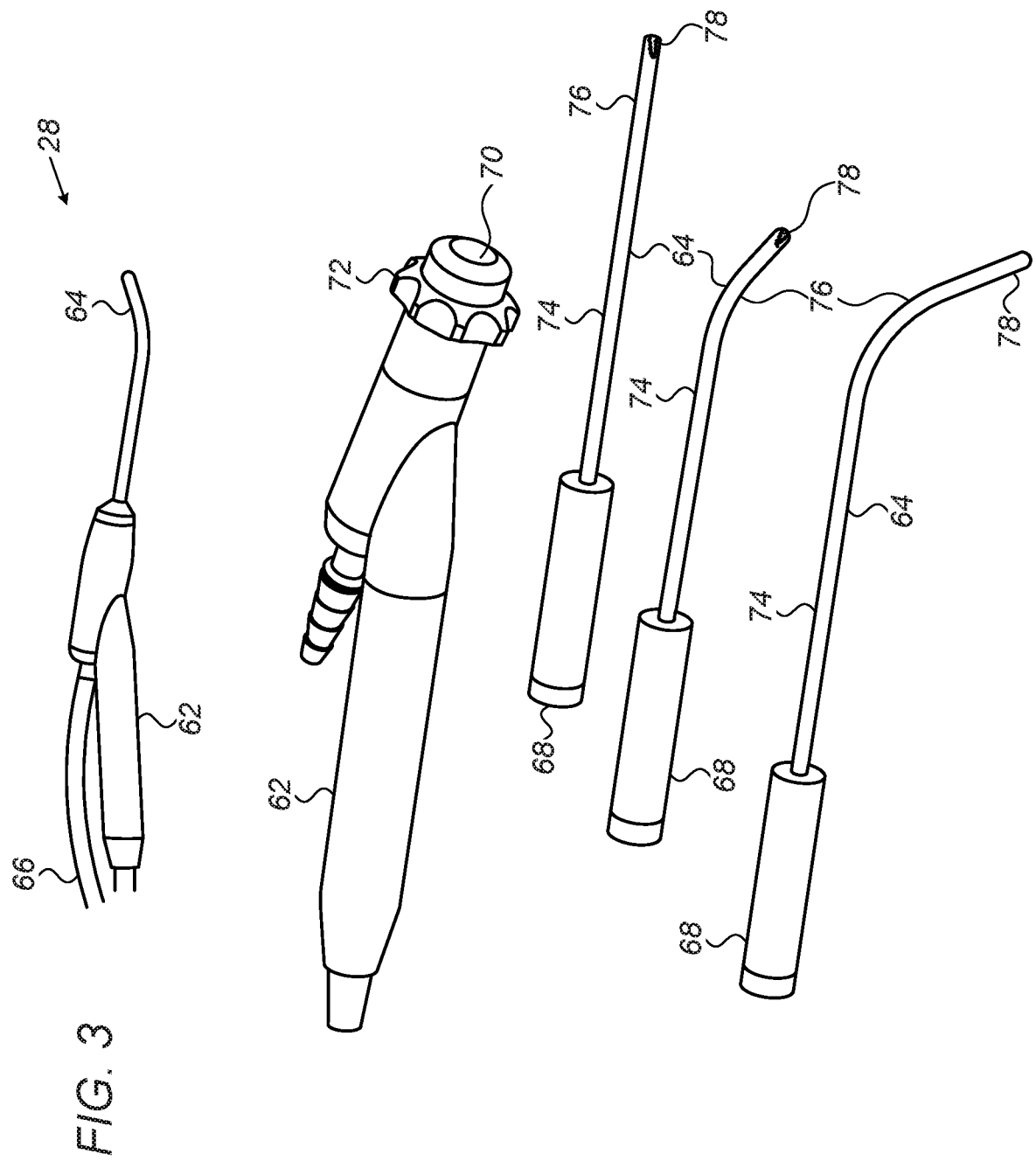

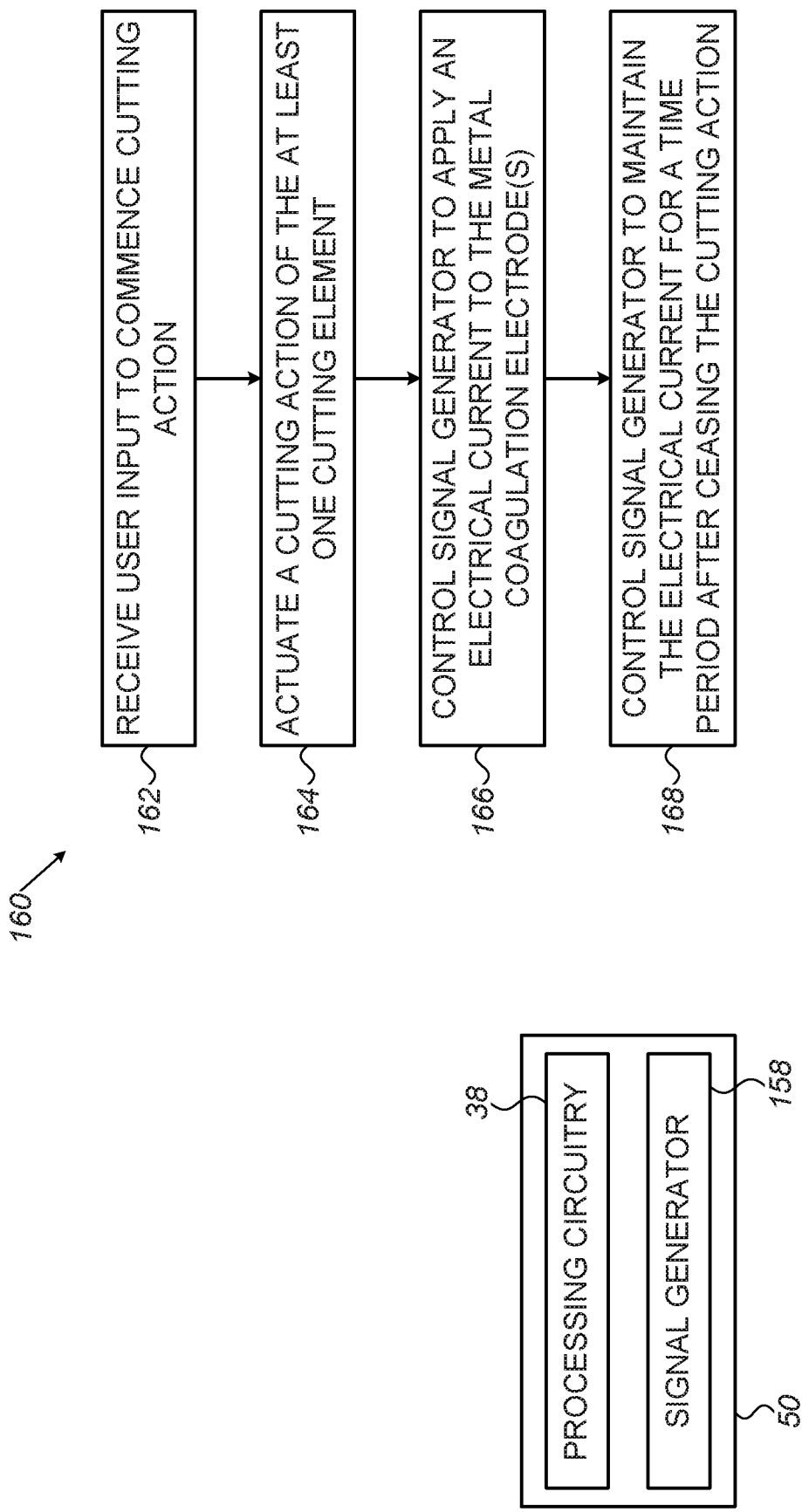

MEDICAL INSTRUMENT WITH COAGULATION

This application is a continuation of U.S. patent application Ser. No. 16/375,198, entitled "Medical Instrument with Coagulation," filed Apr. 4, 2019, and issued as U.S. Pat. No. 11,272,980 on Mar. 15, 2022.

FIELD OF THE INVENTION

The present invention relates to medical devices, and in particular, but not exclusively to, devices which perform coagulation.

BACKGROUND

Shavers or debriders may be used in medical applications to perform cutting of tissue which generally results in massive bleeding. Coagulation in surgical procedures may be performed by applying an electrical current to the bleeding tissue. By way of example, U.S. Pat. No. 5,810,809 to Rydell describes an arthroscopy instrument for debriding tissue which includes an electrocautery electrode for effecting hemostasis in a surgical site. A drive motor for the debriding instrument is placed remotely from the instrument's handle and provision is made for electrically insulating the handle from the drive motor and associated power supply even though the arthroscopic surgery is taking place under saline.

U.S. Pat. No. 8,702,702 to Edwards, et al., describes a mechanical cutting device that makes use of mechanical (rotary) motion and suction to engage tissue and also applies a cutting energy sufficient to vaporize the tissue. The rotation and suction are used to engage the tissue (sucking tissue into cutting windows when the cutting windows of inner and outer blades are aligned), and then the cutting member(s) function as an electrode(s) by having an electrical cutting signal applied thereto so that the cutting member(s) electrically cut the tissue as the cutting members relatively rotate. The electrical cutting signal is only applied as the windows become aligned up until the cutting of the tissue is completed. The cutting signal preferably is stopped after the cutting windows become misaligned. While the cutting windows are misaligned, a coagulation signal can be supplied to the cutting member so that the device functions as an electrocautery device.

US Patent Publication 2014/0148729 of Schmitz, et al., describes a method for removing at least part of a brain tumor and may first involve contacting a forward-facing tissue cutter disposed at the distal end of a tissue removal device with the brain tumor. The tissue removal device may include a shaft having a diameter no greater than about 10 mm, and in some embodiments the tissue cutter does not extend laterally beyond the diameter of the shaft. The method may next involve cutting tissue from the brain tumor, using the tissue cutter. The method may then involve moving the cut tissue through a channel of the shaft in a direction from the distal end of the tissue removal device toward a proximal end of the device.

SUMMARY

There is provided in accordance with an embodiment of the present disclosure, a medical system, including a medical instrument including an elongated shaft having a distal end, at least one cutting element disposed at a distal end of the shaft, a position-tracking transducer disposed at the distal end of the shaft, and electrically insulated from the shaft and the at least one cutting element, and at least one metal coagulation electrode disposed at least partially over the position-tracking transducer, which electrically isolates the at least one metal coagulation electrode from the shaft, a signal generator coupled to apply an electrical current to the at least one metal coagulation electrode, and processing circuitry configured to receive signals generated by the position-tracking transducer, and track a location of the distal end responsively to the received signals.

Further in accordance with an embodiment of the present disclosure the processing circuitry is configured to control the signal generator to apply the electrical current to the at least one metal coagulation electrode responsively to actuation of a cutting action by the at least one cutting element.

Still further in accordance with an embodiment of the present disclosure the processing circuitry is configured to control the signal generator to maintain the electrical current applied to the at least one metal coagulation electrode for a time period after ceasing the cutting action.

Additionally, in accordance with an embodiment of the present disclosure the at least one metal coagulation electrode includes a first metal coagulation electrode and a second metal coagulation electrode, wherein the signal generator is coupled to apply the electrical current between the first and second metal coagulation electrodes.

Moreover, in accordance with an embodiment of the present disclosure the signal generator is coupled to apply the electrical current between the at least one metal coagulation electrode and the at least one cutting element.

Further in accordance with an embodiment of the present disclosure the signal generator is coupled to apply the electrical current between the at least one metal coagulation electrode and at least one head surface electrode.

Still further in accordance with an embodiment of the present disclosure the at least one metal coagulation electrode includes a metal ring wrapped around the shaft.

Additionally, in accordance with an embodiment of the present disclosure the at least one metal coagulation electrode covers at least 90% of an outward facing surface area of the position-tracking transducer.

Moreover, in accordance with an embodiment of the present disclosure the position-tracking transducer include at least one coil.

Further in accordance with an embodiment of the present disclosure the at least one coil is printed on a circuit board, the at least one coil being coated with an electrically insulating material.

Still further in accordance with an embodiment of the present disclosure the medical instrument is configured for inserting into a body part of a living subject, the system further including a location pad having at least one magnetic field radiator configured to transmit alternating magnetic fields into a region where the body-part is located, the at least one coil of the position-tracking transducer being configured to detect at least part of the transmitted alternating magnetic fields.

Additionally in accordance with an embodiment of the present disclosure the medical instrument is configured for inserting into a body part of a living subject, the system further including a display, the processing circuitry being configured to render to the display an image including a representation of at least part of the body part and a representation of at least part of the medical instrument inserted in the body part responsively to the tracked location.

There is also provided in accordance with another embodiment of the present disclosure a method for medical treatment using a medical instrument including an elongated shaft having a distal end, at least one cutting element disposed at a distal end of the shaft, a position-tracking transducer disposed at the distal end of the shaft, and electrically insulated from the shaft and the at least one cutting element, and at least one metal coagulation electrode disposed at least partially over the position-tracking transducer, which electrically isolates the at least one metal coagulation electrode from the shaft, the method including applying an electrical current to the at least one metal coagulation electrode, receiving signals generated by the position-tracking transducer, and tracking a location of the distal end responsively to the received signals.

Moreover, in accordance with an embodiment of the present disclosure the applying is performed responsively to actuation of a cutting action by the at least one cutting element.

Further in accordance with an embodiment of the present disclosure, the method includes maintaining the electrical current applied to the at least one metal coagulation electrode for a time period after ceasing the cutting action.

Still further in accordance with an embodiment of the present disclosure the at least one metal coagulation electrode includes a first metal coagulation electrode and a second metal coagulation electrode, wherein the applying includes applying the electrical current between the first and second metal coagulation electrodes.

Additionally, in accordance with an embodiment of the present disclosure the applying includes applying the electrical current between the at least one metal coagulation electrode and the at least one cutting element.

Moreover, in accordance with an embodiment of the present disclosure the applying includes applying the electrical current between the at least one metal coagulation electrode and at least one head surface electrode.

Further in accordance with an embodiment of the present disclosure the at least one metal coagulation electrode includes a metal ring wrapped around the shaft.

Still further in accordance with an embodiment of the present disclosure the at least one metal coagulation electrode covers at least 90% of an outward facing surface area of the position-tracking transducer.

Additionally, in accordance with an embodiment of the present disclosure the position-tracking transducer include at least one coil.

Moreover, in accordance with an embodiment of the present disclosure the at least one coil is printed on a circuit board, the at least one coil being coated with an electrically insulating material.

Further in accordance with an embodiment of the present disclosure the medical instrument is configured for inserting into a body part of a living subject, the method further including transmitting alternating magnetic fields into a region where the body-part is located, and detecting at least part of the transmitted alternating magnetic fields by the at least one coil.

Still further in accordance with an embodiment of the present disclosure the medical instrument is configured for inserting into a body part of a living subject, the method further including rendering to a display an image including a representation of at least part of the body part and a representation of at least part of the medical instrument inserted in the body part responsively to the tracked location.

BRIEF DESCRIPTION OF THE DRAWINGS

The present invention will be understood from the following detailed description, taken in conjunction with the drawings in which:

FIG. 3 is a schematic view of a medical instrument for use in the system of FIG. 1;

FIG. 4 shows a handle and interchangeable heads of the medical instrument of FIG. 3;

FIG. 10 is a block diagram view of part of the console of the medical procedure system of FIG. 1 in accordance with an alternative embodiment of the present invention; and FIG. 11 is a flowchart including exemplary steps in a coagulation method performed by the medical procedure system of FIG. 1.

DESCRIPTION OF EXAMPLE EMBODIMENTS

Overview

Figure 1:
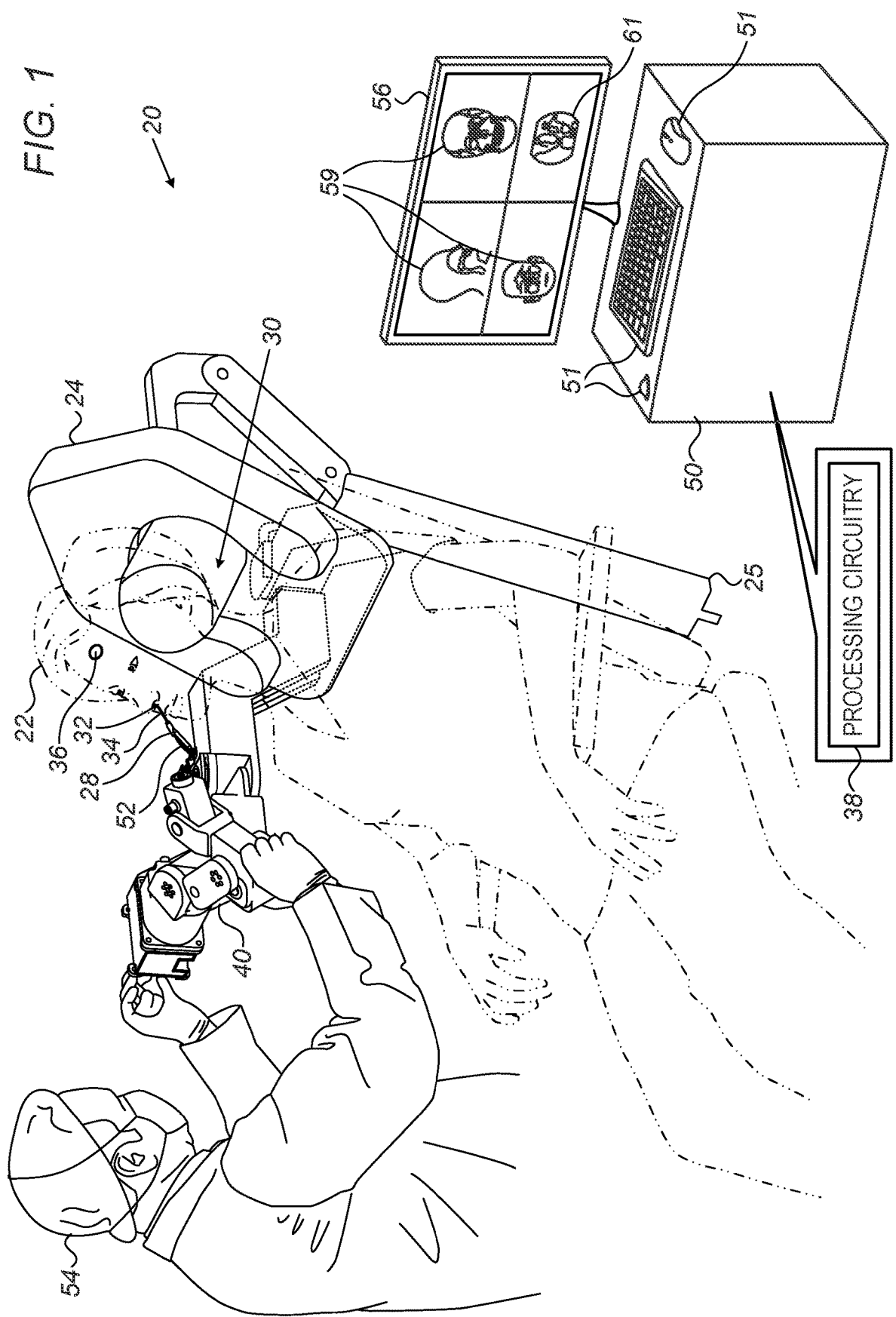
FIG. 1 is a schematic illustration of a medical procedure system, according to an embodiment of the present invention.

As mentioned above, shavers or debriders may be used in medical applications to perform cutting of tissue which generally results in massive bleeding. Coagulation in surgical procedures may be performed by applying an electrical current to the bleeding tissue.

Performing coagulation with a medical instrument may be complicated by the geometry and mechanical structure of the medical instrument. For example, if a medical instrument includes many conducting surfaces, applying an electrical current may be limited due to inherent short circuits caused by the metal surfaces. Adding further non-conducting structures to the medical instrument may add too much bulk to the medical instrument.

Embodiments of the present invention provide a medical system including a medical instrument having an elongated shaft having a distal end, at least one cutting element disposed at a distal end of the shaft, and a position-tracking transducer disposed at the distal end of the shaft. The medical instrument is generally inserted into a body part of a living subject to cut tissue from the body part.

Processing circuitry receives signals generated by the position-tracking transducer and tracks a location of the distal end responsively to the received signals. The processing circuitry also renders to a display an image including a representation of at least part of the body part and a representation of at least part of the medical instrument inserted in the body part responsively to the tracked location.

The position-tracking transducer may include at least one coil by way of example only. In some embodiments the position-tracking transducer may include two or more orthogonally placed coils.

In some embodiments, a location pad having at least one magnetic field radiator transmits alternating magnetic fields into a region where the body-part is located. The coil(s) of the position-tracking transducer detect at least part of the transmitted alternating magnetic fields. The position of the distal end may then be tracked based on signals output by the position-tracking transducer. In other embodiments, the position of the distal end may be tracked using any suitable position tracking system, for example, but not limited to, electric-current-based, or ultrasound-based position tracking.

The coil(s) may be printed on a printed circuit board and the coil(s) may be coated with an electrically insulating material. There are several advantages of using a PCB transducer. First, a PCB transducer does not suffer from metal interference which is important when the medical instrument includes metal elements. Second, the PCB may be placed very accurately orientation-wise on the distal end of the shaft. Third, the PCB transducer is not a wound coil, but is a printed coil, so that each PCB has substantially the same magnetic sensitivity. Therefore, based on the above advantages the PCB transducer does not generally need calibration and does not need a controller (e.g., an EEPROM) which is generally too bulky for disposing on the distal end.

The position-tracking transducer is electrically insulated from the shaft and the cutting element(s), for example, by the PCB and the coating applied to the coil(s).

The medical instrument also includes at least one metal coagulation electrode disposed at least partially over the position-tracking transducer, which electrically isolates the metal coagulation electrode(s) from the shaft.

In addition to the position-tracking transducer providing electrical isolation between the metal coagulation electrode(s) and the shaft, the metal coagulation electrode provides a certain amount of electromagnetic shielding to the position-tracking transducer. The location pad mentioned above typically transmits magnetic fields at a lower frequency (for example, around 20 KHz) whereas background radiation may be in the radio wave spectrum. The metal coagulation electrode(s) helps to filter out the higher radio wave spectrum frequencies from the frequencies detected by the position-tracking transducer. This filtering is particularly advantageous when the signals output by the position-tracking transducer are processed by an analogue-to-digital converter at a high frequency.

In some embodiments, the metal coagulation electrode(s) includes one or more metal rings wrapped around the shaft. In some embodiments, the metal coagulation electrode(s) covers at least 90% of an outward facing surface area of the position-tracking transducer.

The system also includes a signal generator coupled to apply an electrical current which may comprise a direct current (DC) or close to DC (e.g., at a low frequency, such as up to 20 Khz, by way of example only) to the metal coagulation electrode(s) which results in coagulation being performed in the region of the cutting element(s) thereby stopping, or at least reducing, bleeding caused from the cutting.

In some embodiments, the processing circuitry controls the signal generator to apply the electrical current to the metal coagulation electrode(s) responsively to actuation of a cutting action by the cutting element(s).

In disclosed embodiments, the processing circuitry controls the signal generator to maintain the electrical current applied to the metal coagulation electrode(s) for a time period (e.g., up to 3 seconds, or in some cases more than 3 seconds) after ceasing the cutting action.

In some embodiments, the metal coagulation electrodes comprise two coagulation electrodes (e.g., two rings wrapped around the shaft) and the signal generator is coupled to apply the electrical current between the two metal coagulation electrodes.

In other embodiments, the signal generator is coupled to apply the electrical current between the metal coagulation electrode(s) and the cutting element(s). In yet other embodiments, the signal generator is coupled to apply the electrical current between the metal coagulation electrode(s) and at least one head surface electrode.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 2:
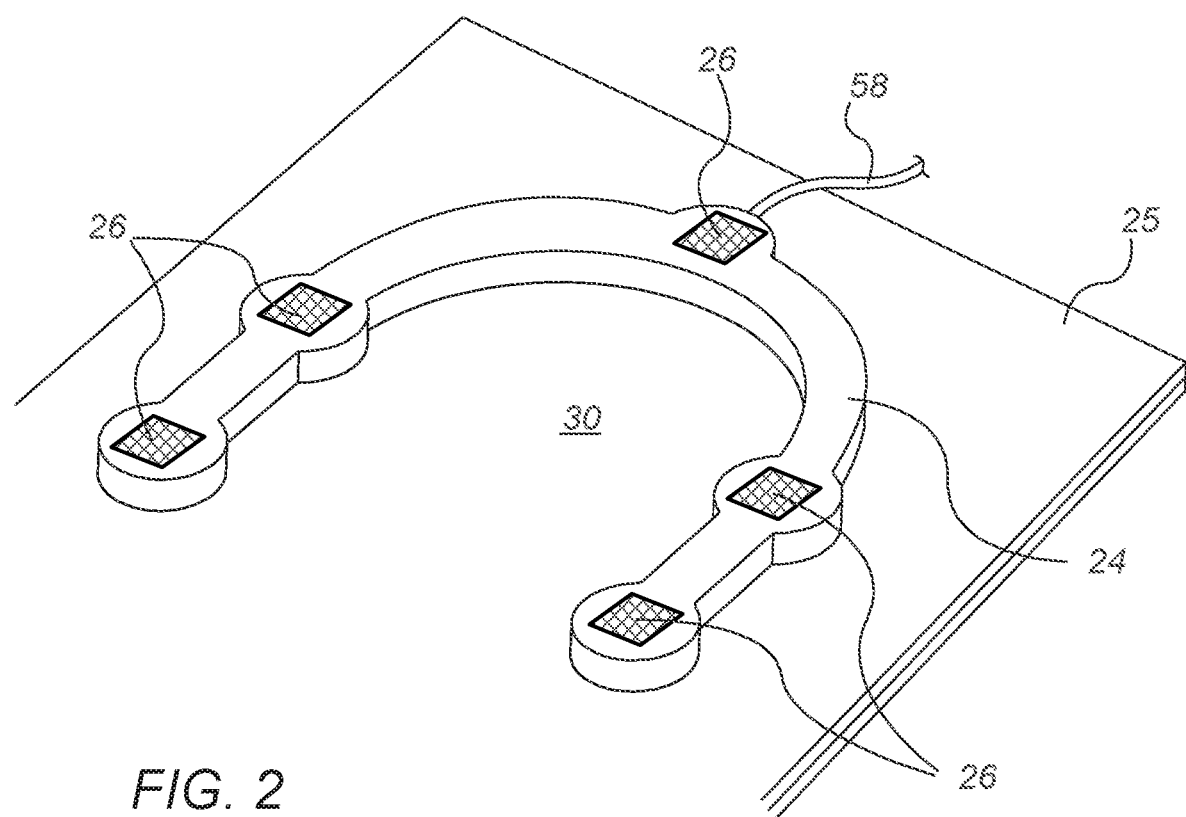
FIG. 2 is a schematic illustration of a magnetic field radiation assembly used in the medical procedure system, according to an embodiment of the present invention.

Turning now to the drawings, reference is now made to FIG. 1, which is a schematic illustration of a medical procedure system 20, and to FIG. 2, which is a schematic illustration of a magnetic field radiation assembly location pad 24 used in the system 20, according to an embodiment of the present invention. The medical procedure system 20 is typically used during an invasive and/or investigative procedure on a nasal sinus or another body part (such as the brain) of a patient 22.

For the procedure, the magnetic field radiation assembly 24 may be positioned behind and/or around the head of the patient 22, for example by fixing the assembly 24 to a chair 25 (or bed) upon which the patient is sitting (or lying). The magnetic field radiation assembly 24 in the pictured example comprises five magnetic field radiators 26, which are fixed in a horseshoe shaped frame, the frame being positioned beneath or around the patient 22 so that the magnetic field radiators 26 surround the head of the patient 22. Alternatively, smaller or larger numbers of radiators 26 may be used, in various different configurations. The magnetic field radiators 26 are configured to radiate alternating magnetic fields at respective frequencies into a region 30 where the body part is located, in proximity to the magnetic field radiation assembly 24 and which includes the head of patient 22.

The alternating magnetic fields induce signals in a position-tracking transducer 32 and a position-tracking transducer 36. The position-tracking transducer 32 is shown disposed on a medical instrument 28 in order to track a position of the medical instrument 28. The position-tracking transducer 36 is shown disposed on the patient 22 (e.g., on the forehead of the patient 22 or any other suitable body part) in order to track a position of the patient 22 (e.g., to track a position of the head of the patient 22) to compensate for movement of the patient with respect to the magnetic field radiation assembly 24. By way of example only, the medical instrument 28 may include any one or more of the following, a probe for inserting into the body-part, an endoscope, and/or a surgical tool such as an ENT tool, suction tool, microdebrider, or a shaver.

The position of the distal end of the medical instrument 28 and the position of the patient 22, may be tracked using a tracking subsystem, which tracks position and orientation coordinates of the position-tracking transducer 32 fitted at the distal end and the position-tracking transducer 36, respectively. The position-tracking transducers 32, 36 are configured to output signals that are indicative of locations of the transducer 32, 36, respectively. The signals are processed by the tracking subsystem running on processing circuitry 38 to track the locations of the distal end of the medical instrument 28 and the position of the patient 22 over time. In embodiments, where the tracking subsystem is a magnetic tracking subsystem, the position-tracking transducer 32 and/or the position-tracking transducer 36 includes at least one coil, described in more detail with reference to FIG. 5. In other embodiments, the tracking subsystem may be an electrically-based tracking subsystem using multiple head surface electrodes (e.g., multiple instances of the position-tracking transducer 36) to track the position of the medical instrument 28 based on a signal emitted by at least one electrode (comprised in the position-tracking transducer 32) of the medical instrument 28. The tracking subsystem may be implemented using any suitable location tracking subsystem, for example, but not limited to, an ultrasound-based tracking system where the position-tracking transducer 32 includes at least one ultrasound transducer. Using tracking subsystem, a physician 54 advances the distal end of the medical instrument 28 in a body-part, described in more detail below.

In some embodiments, the medical instrument 28 is attached to, and held by, a robotic arm 40, which is configured to manipulate the medical instrument 28. The robotic arm 40 includes a plurality of robotic joints configured to control movement of the robotic arm 40 and manipulate the medical instrument 28. In other embodiments, the medical instrument 28 is held and manipulated by the physician 54.

As is described in more detail below, position-tracking transducer 32 is affixed to the medical instrument 28, and determination of the location and orientation of the position-tracking transducer 32 enables tracking the location and orientation of a distal end 34 (or other location) of the medical instrument 28, that may be reversibly inserted into a body-part of the patient 22 (the living subject).

Similarly, determination of the location and orientation of the position-tracking transducer 36 enables the location and orientation of a part (e.g., the head) of the patient 22 to be tracked. The position-tracking transducer 36 is shown in FIG. 1 as being disposed on the forehead of the patient 22. The position-tracking transducer 36 may be disposed on any other suitable body part of the patient 22 in order to track the position/movement of the patient 22.

A system using magnetic field radiators, such as the magnetic field radiators 26, for tracking an entity inserted into a patient is described in US Patent Publication 2016/0007842, of Govari et al., issued as U.S. Pat. No. 10,772,489 on Sep. 15, 2020, which is incorporated herein by reference. In addition, the Carto® system produced by Biosense Webster of 33 Technology Drive, Irvine, Calif. 92618 USA, uses a tracking system similar to that described herein for finding the location and orientation of a coil in a region irradiated by magnetic fields.

The robotic arm 40 generally has its own robotic coordinate system. The robotic coordinate system is registered with a magnetic coordinate system of the magnetic field radiators 26 or vice-versa. Registration of the robotic coordinate system with the magnetic coordinate system may be performed, for example, by moving the robotic arm 40, or the medical instrument 28 attached to the robotic arm 40, to one or more locations known to the magnetic field radiators 26, for example, to a location on the magnetic field radiation assembly 24 or to the position-tracking transducer 36 or to one or more other known locations on the patient 22. Once registration of the robotic coordinate system with the magnetic coordinate system has been performed, locations in the magnetic coordinate system can be translated to the robotic coordinate system in order to manipulate the robotic arm 40 correctly.

Elements of system 20, including radiators 26, may be controlled by the processing circuitry 38, which comprises a processing unit communicating with one or more memories. Typically, the elements may be connected by cables to the processing circuitry 38, for example, radiators 26 may be connected by a cable 58 to the processing circuitry 38. Alternatively, or additionally, the elements may be coupled wirelessly to the processing circuitry 38. The processing circuitry 38 may be mounted in a console 50, which comprises operating controls 51 that typically include a keypad and/or a pointing device such as a mouse or trackball. The console 50 also connects to other elements of the medical procedure system 20, such as a proximal end 52 of the medical instrument 28. A physician 54 uses the operating controls 51 to interact with the processing circuitry 38 while performing the procedure, and the processing circuitry 38 may present results produced by system 20 on a display 56.

In some embodiments, prior to performing the medical procedure, CT images of the patient 22 are acquired. The CT images are stored in a memory (not shown) for subsequent retrieval by the processing circuitry 38. In FIG. 1, the display 56 is shown displaying various views 59 of a previous CT scan (or other suitable scan) which may be used as an aid for the physician 54 to guide the medical instrument 28 in the body-part. The display screen 56 also shows an image 61 captured by a camera (not shown) of the medical instrument 28. The CT images may be registered with the magnetic coordinate system so that a representation of the medical instrument 28 may be displayed with the CT images on the display 56 as will be described in more detail with reference to FIGS. 7 and 8.

In practice, some or all of these functions of the processing circuitry 38 may be combined in a single physical component or, alternatively, implemented using multiple physical components. These physical components may comprise hard-wired or programmable devices, or a combination of the two. In some embodiments, at least some of the functions of the processing circuitry may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

Reference is now made to FIG. 3, which is a schematic view of the medical instrument 28 for use in the system 20 of FIG. 1. The medical instrument 28 includes a handle 62 in which a plurality of different rigid interchangeable heads 64 are individually reversibly insertable. FIG. 3 shows one of the interchangeable heads 64 inserted into the handle 62. Other ones of the interchangeable heads 64 are shown in FIG. 4, which is described hereinbelow. The medical instrument 28 shown in FIG. 3 also includes an irrigation or drainage tube 66.

The medical instrument 28 shown in FIG. 3 is shown prior to any position-tracking transducers being added to the medical instrument 28. In fact, in some embodiments, the medical instrument 28 may be implemented with an off-the-shelf medical instrument which is sold without position transducers or sensors and to which position-tracking transducers are added at appropriate positions, as will be described below with reference to FIG. 5. For example, the S120 hand-piece and interchangeable reusable blades of Bien Air®, which is available without position transducers, may be adapted to provide the medical instrument 28 described hereinbelow. In other embodiments, the medical instrument 28 may be implemented as a purpose-built medical instrument with integral position-tracking transducers.

Reference is now made to FIG. 4, which shows the handle 62 and multiple different interchangeable heads 64 of the medical instrument 28 of FIG. 3. The handle 62 and the interchangeable heads 64 shown in FIG. 4 are also shown without the position-tracking transducers. The interchangeable heads 64 are different from each other with respect to a head shape and/or a head size.

Each interchangeable head 64 includes a plastic proximal end 68 which is inserted into a socket 70 of the handle 62. The socket 70 of the handle 62 includes multiple rotational positions in which to insert the different rigid interchangeable heads 64. For example, with the S120 hand-piece, the reusable blades may be inserted in eight different rotational positions. In some embodiments, the interchangeable heads 64 may be inserted into the socket 70 in a single rotational position.

The handle 62 includes multiple rotational positions to which to rotate the different rigid interchangeable heads 64. Therefore, once one of the interchangeable heads 64 has been inserted into the socket 70, the inserted interchangeable head 64 may be rotated to multiple rotational positions using a rotational adjustment cog wheel 72. In other embodiments, the inserted interchangeable head 64 cannot be rotated to another position.

In the example of FIG. 4, each of the interchangeable heads 64 is implemented with an elongated shaft 74 having a distal end 76, which includes at least one cutting element 78 disposed at the distal end 76 of the elongated shaft 74. The cutting element(s) 78 may include a shaving bur (e.g., a rough surface cylindrical shape or ball shape element) or a shaving blade rotating inside the elongated shaft 74 or any other suitable cutting element.

Figure 5:
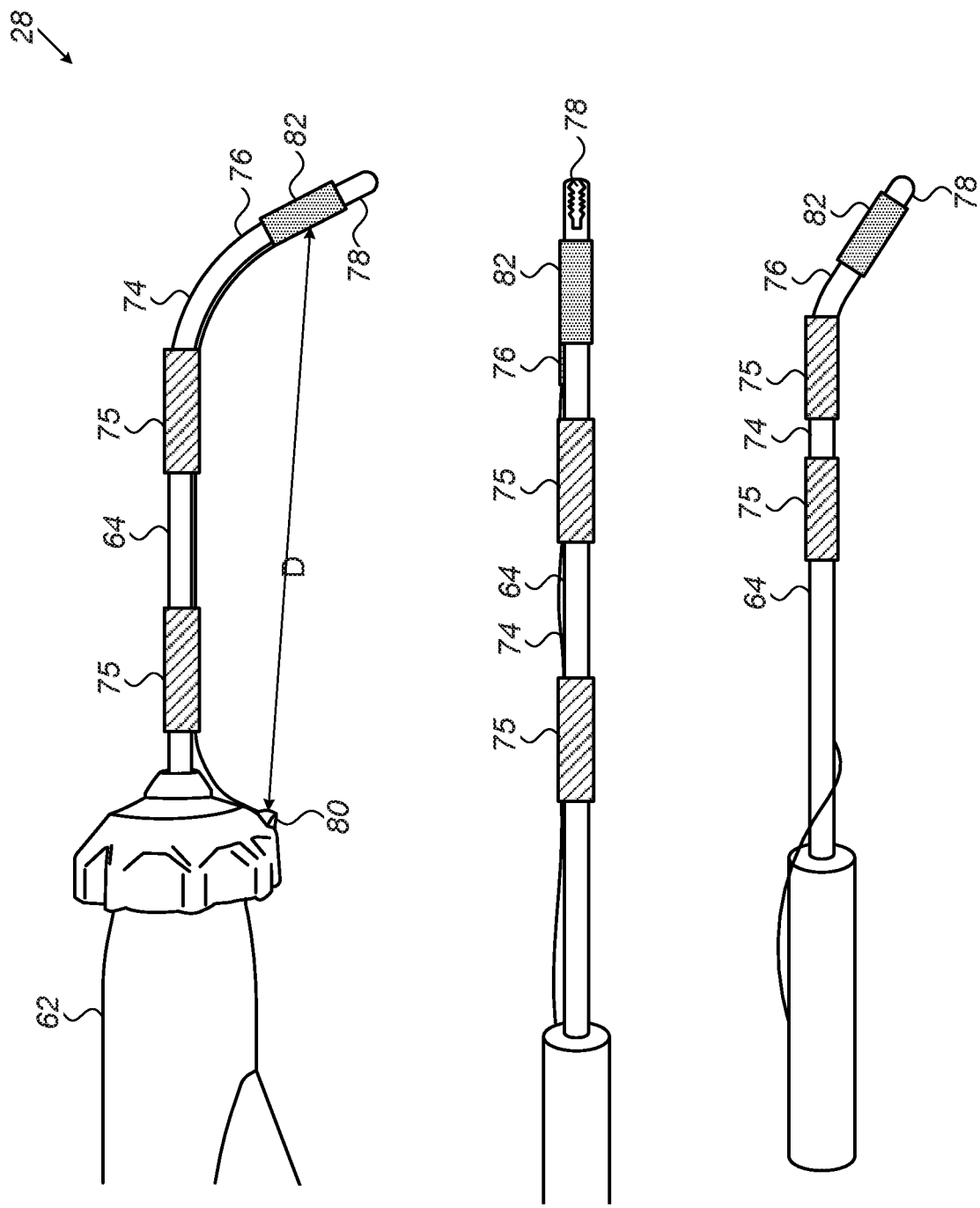
FIG. 5 shows transducers disposed on the handle and interchangeable heads of the medical instrument of FIG. 3.

Reference is now made to FIG. 5, which shows transducers 80, 82 disposed on the handle 62 and interchangeable heads 64 of the medical instrument 28 of FIG. 3. The handle 62 has a handle position-tracking transducer 80 disposed thereon. The handle position-tracking transducer 80 may include a dual or triple axis transducer, which can be used to detect a location, and orientation (including roll) of the handle 62. In some embodiments, the handle position-tracking transducer 80 may include at least one coil, for example two or three orthogonally placed coils.

Each interchangeable head 64 includes a head position-tracking transducer 82 disposed thereon at the distal end 76 of the elongated shaft 74 of the interchangeable head 64. The head position-tracking transducer 82 is electrically insulated from the elongated shaft 74 and the cutting element(s) 78. Wires extending from the head position tracking transducer 82 are secured, for example using self-adhesive tape 75, to the elongated shaft 74.

In some embodiments, the head position-tracking transducer 82 of each interchangeable head 64 may include at least one coil. The head position-tracking transducer 82 of each interchangeable head 64 may include a dual-axis transducer (for example, comprising two orthogonally placed coils) which can be used to detect a location, and orientation (including roll) of that interchangeable head 64. The head position-tracking transducer 82 may be printed on one or two printed circuit boards. For example, two coils may be printed on one or two printed circuit boards which are connected to the distal end 76 of the elongated shaft 74 so that each of the coils is orthogonal to the other. Printing the coils onto printed circuit board provides a more compact and more standard transducer than using wound coils. The coils may be coated with an electrically insulating material.

The handle position-tracking transducer 80, and the head position-tracking transducer 82 of each interchangeable head 64, are configured to detect at least part of the transmitted alternating magnetic fields of the magnetic field radiators 26 (FIG. 2).

At least some of the elongated shaft 74 may disposed in a plastic biocompatible sleeve prior to inserting the elongated shaft 74 in a body part. In some embodiments, the sleeve may cover the elongated shaft 74 from the plastic proximal end 68 up to and including the head position-tracking transducer 82.

The head position-tracking transducers 82 are strategically placed on the interchangeable heads 64 so that when each interchangeable head 64 is individually inserted into the handle 62, the relative position between the handle position-tracking transducer 80 and the head position-tracking transducer 82 of the inserted interchangeable head 64 uniquely identifies the inserted interchangeable head 64 irrespective of the rotational position in which the interchangeable head 64 has been inserted into the handle 62 and irrespective of the rotational position to which the interchangeable head 64 has been rotated. The relative position may include: (i) a distance D between the handle position-tracking transducer 80 and one of the head position-tracking transducers 82; and/or (ii) a relative orientation (which may or may not include roll) between the handle position-tracking transducer 80 and one of the head position-tracking transducers 82.

Therefore, different respective ones of the interchangeable heads 64 having differently positioned respective head position-tracking transducers 82 disposed thereon (on the distal end 76 of the respective head 64) so as when the different respective ones of the interchangeable heads 64 are inserted into the handle 62, the different respective head position-tracking transducers 82 define different respective positions relative to the handle position-tracking transducer 80.

Figure 6:
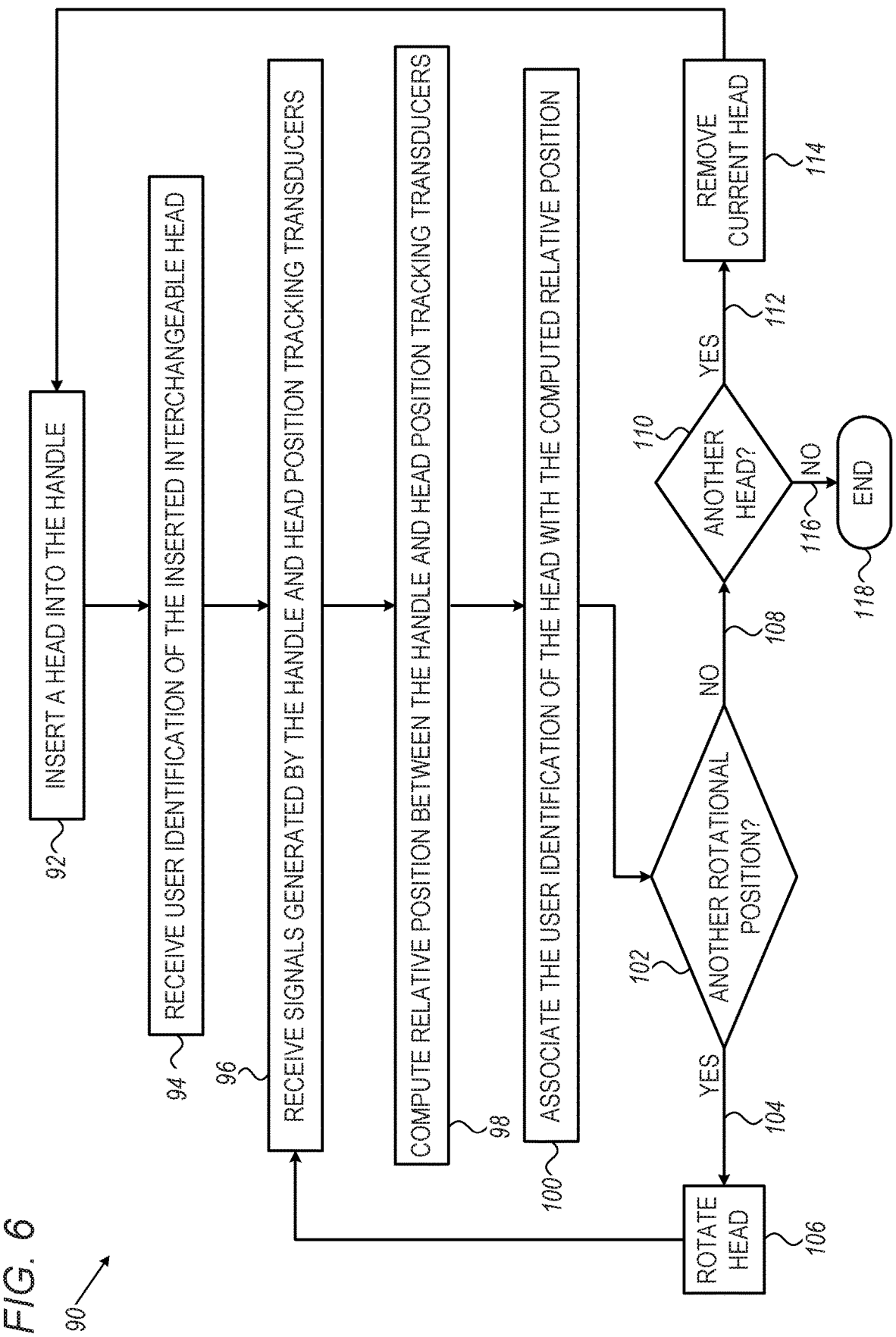
FIG. 6 is a flowchart including exemplary steps in a calibration method of the medical instrument of FIG. 5.

Reference is now made to FIG. 6, which is a flowchart 90 including exemplary steps in a calibration method of the medical instrument 28 of FIG. 5. Reference is also made to FIG. 5. One of the interchangeable heads 64 is inserted (block 92) into the handle 62. The processing circuitry 38 is configured to receive (block 94) a user identification of the inserted interchangeable 64 head via a user input device (e.g., the operating controls 51 (FIG. 1).

The processing circuitry 38 (FIG. 1) is configured to receive (block 96) signals generated by the handle position-tracking transducer 80 and the respective head position-tracking transducer 82 of the respective one of the interchangeable heads 64 inserted into the handle 62. The processing circuitry 38 is configured to compute (block 98) a relative position between the handle position-tracking transducer 80 and the head position-tracking transducer 82 of the inserted interchangeable head 64 responsively to the received signals. The computed relative position may include: (i) a computed distance D between the handle position-tracking transducer 80 and the head position-tracking transducer 82 of the inserted interchangeable head 64; and/or (ii) a computed relative orientation (which may or may not include roll) between the handle position-tracking transducer 80 and the head position-tracking transducer 82 of the inserted interchangeable head 64.

The processing circuitry 38 is configured to associate (block 100) the user identification of the inserted interchangeable head 64 with the computed relative position (e.g., the computed distance and/or the computed relative orientation) so as to allow future identification of the inserted interchangeable head 64 being reinserted into the handle responsively to a new computed relative position (e.g., a new computed distance and/or a new computed relative orientation) being within a given tolerance of the computed relative position (e.g., the computed distance and/or the computed relative orientation). The given tolerance may be any suitable value, for example, the given tolerance may be in the range of 0.1 mm to 5 mm and/or an angular orientation tolerance of up to 5 or 10%.

At a decision block 102, the processing circuitry 38 renders a question to the display 56 asking the user whether there is another rotational position in which to insert the interchangeable head 64 or to which to rotate the inserted interchangeable head 64. The user provides a response via the operating controls 51 for receipt by the processing circuitry 38. If the user responds that there is another rotational position (branch 104), the user rotates (block 106) the inserted interchangeable head 64 to a new rotational position and the method continues with the step of block 96. When the inserted interchangeable head 64 may be rotated freely with respect to the handle 62, the user may indicate this to the response of the rendered question at the step of block 102 and then continuously rotate the inserted interchangeable head 64 while the steps of blocks 96 to 100 are repeated for the different rotational positions of the inserted interchangeable head 64. If the user responds that there are no more rotational positions (branch 108), the processing circuitry 38 renders (block 110) a question to the display 56 asking the user whether there are more interchangeable heads 64 to calibrate. The user responds to the question. If there are more interchangeable heads 64 to calibrate (branch 112), the current head is removed (block 114) and a new interchangeable head 64 is inserted in the step of block 92 and the steps in the flowchart 90 are followed as described above. If there are no more interchangeable heads 64 to calibrate (branch 116) the method ends (block 118).

The above calibration method may include an additional step to check whether the computed relative position between the handle position-tracking transducer 80 and the head position-tracking transducer 82 for an inserted interchangeable head 64 is the same as, or within a given tolerance of, a previously computed relative position between the handle position-tracking transducer 80 and the head position-tracking transducer 82 of another one of the interchangeable heads 64. If the computed relative position, is the same as, or within a given tolerance of, the previously computed relative position between the handle position-tracking transducer 80 and the head position-tracking transducer 82 of another one of the interchangeable heads 64, the processing circuitry 38 may render a message to the display 56 informing the user that the current placement of the head position-tracking transducer 82 should be changed.

The calibration data is saved in a table for later use during operation of the system 20 described below with reference to FIG. 7.

Figure 7:
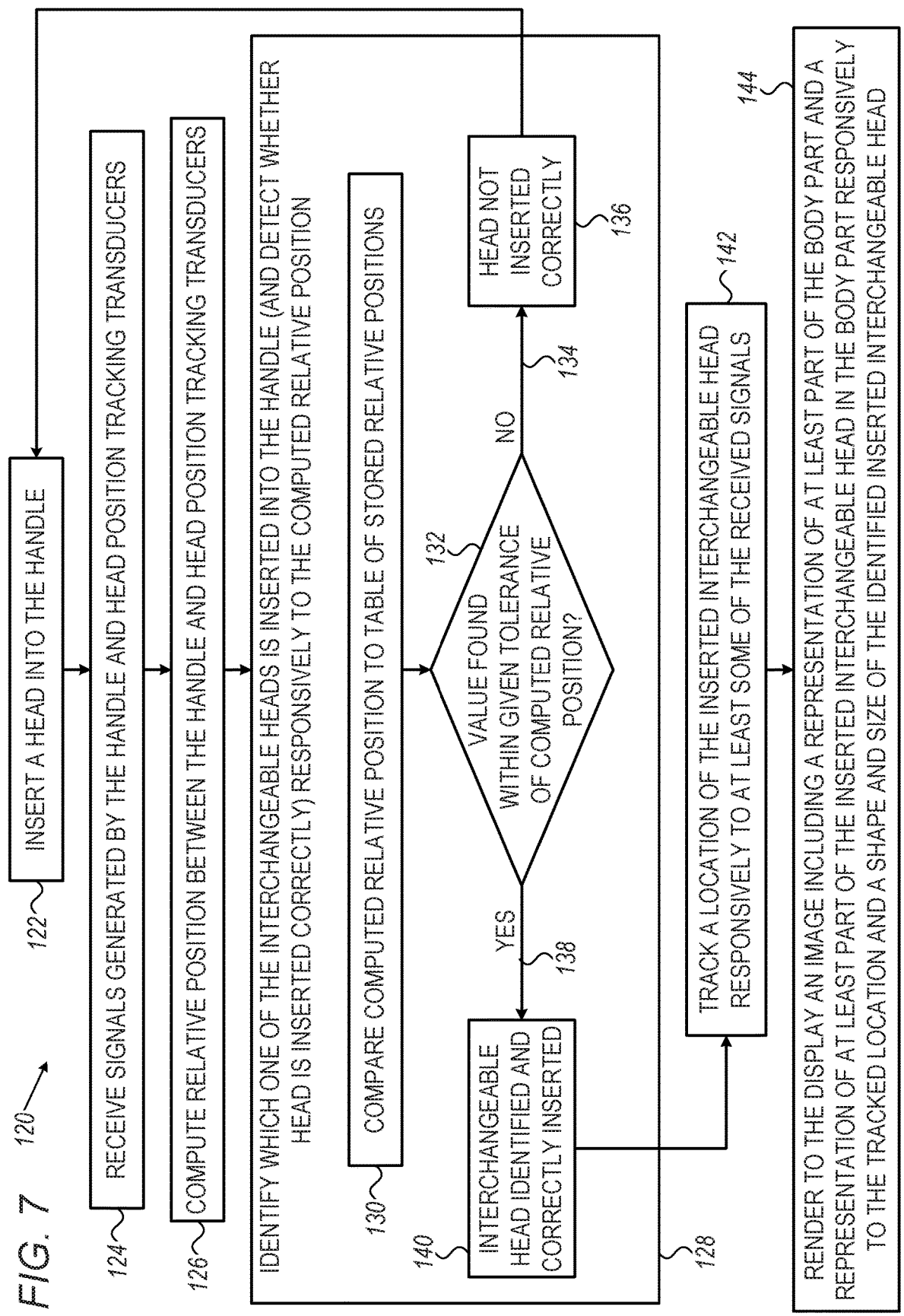
FIG. 7 is a flowchart including exemplary steps in a method of operation of the medical procedure system of FIG. 1.

Reference is now made to FIG. 7, which is a flowchart 120 including exemplary steps in a method of operation of the medical procedure system 20 of FIG. 1. Reference is also made to FIG. 5. The physician 54 inserts (block 122) one of the interchangeable heads 64 into the handle 62. The processing circuitry 38 (FIG. 1) is configured to receive (block 124) signals generated by the handle position-tracking transducer 80 and the respective head position-tracking transducer 82 of a respective one of the interchangeable heads 64 inserted into the handle. The processing circuitry 38 is configured to compute (block 126) a relative position (e.g., distance and/or orientation) between the handle position-tracking transducer 80 and the head position-tracking transducer 82 of the inserted interchangeable head 64 responsively to the received signals. The processing circuitry 38 is configured to identify (block 128) which one of the interchangeable heads 64 is inserted into the handle responsively to the computed relative position (e.g., distance and/or orientation) and optionally whether the interchangeable head 64 is inserted correctly into the handle 62 responsively to the computed relative position. The step of block 128 includes sub-steps now described below.

The processing circuitry 38 is configured to compare (block 130) the computed relative position to values in the table of stored relative positions and associated interchangeable heads 64. At a decision block 132, the processing circuitry 38 determines whether the table includes a value that is within a given tolerance of the computed relative position. If there is not a value (branch 134) in the table within a given tolerance of the computed relative position, the processing circuitry 38 may render (block 136) a message to the display 56 indicating that the interchangeable head 64 is not recognized or is not inserted into the handle 62 correctly. Processing then continues with the step of block 122.

If there is a value (branch 138) in the table within a given tolerance of the computed relative position, the interchangeable head 64 is identified (block 140) as the interchangeable head 64 associated with the value in the table and the inserted interchangeable head 64 is identified as being correctly inserted into the handle 62.

The processing circuitry 38 is configured to track (block 142) a location of the inserted interchangeable head 64 responsively to at least some of the received signals. The signals used to track the location of the inserted interchangeable head 64 may be based on the signals received from the handle position-tracking transducer 80 and/or the signals received from the head position-tracking transducer 82 of the inserted interchangeable head 64. When the interchangeable heads 64 may be rotated freely, for example, using the cog wheel 72 (FIG. 4), the location of the inserted interchangeable head 64 is generally tracked based at least on the signals received from the head position-tracking transducer 82 of the inserted head 64.

Figure 8:
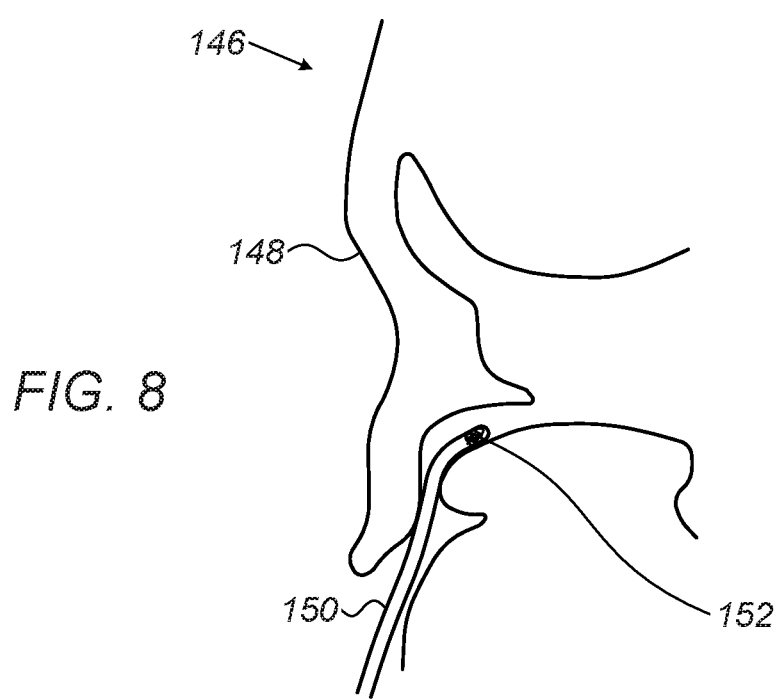
FIG. 8 is a schematic view of an image of a representation of a body part and an inserted interchangeable head rendered by the medical procedure system of FIG. 1.

Reference is now made to FIG. 8, which is a schematic view of an image 146 of a representation 148 of a body part and a representation 150 of an inserted interchangeable head 64 rendered by the medical procedure system 20 of FIG. 1. Reference is also made to FIGS. 5 and 7. The processing circuitry 38 is configured to render (block 144) to the display 56 (FIG. 1) the image 146 including the representation 148 of at least part of the body part and the representation 150 of at least part of the inserted interchangeable head 64 of the medical instrument 28 in the body part responsively to the tracked location and a shape and size of the identified inserted interchangeable head 64. As the interchangeable heads 64 are rigid, the representation 150 of the inserted interchangeable head 64 may be rendered based on a position of a single point of the inserted interchangeable head 64 and a known shape and size of the identified inserted interchangeable head 64. The cutting element(s) 78 may also be indicated using an indicator 152 on the representation 150.

In some embodiments, the steps of blocks 142 and 144 of FIG. 7 may be performed even if the inserted interchangeable head 64 is manually identified to the system 20 by the physician 54, or even if the medical instrument 28 does not have heads which are interchangeable or removable, and/or even if the head(s) is not rigid, and/or even if the head(s) includes multiple sensors which enable rendering the representation 150 of the head 64 based on multiple sensors not necessarily based on a known size and shape of the head 64.

Figure 9A:
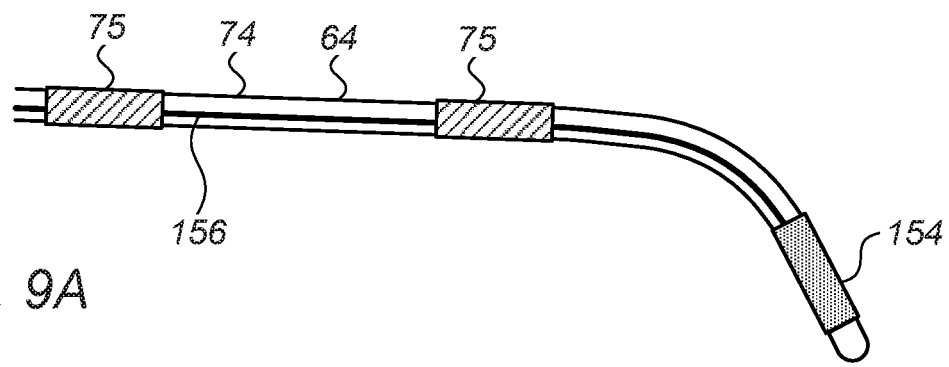
FIGS. 9A and 9B are schematic views of interchangeable heads of the medical instrument of FIG. 5 with metal coagulation electrodes disposed thereon.
Figure 9B:
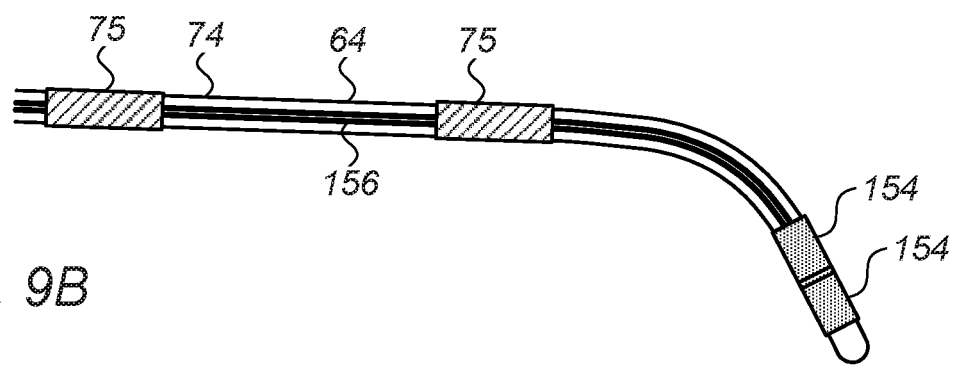

Reference is now made to FIGS. 9A and 9B, which are schematic views of interchangeable heads 64 of the medical instrument 28 of FIG. 5 with metal coagulation electrodes 154 disposed thereon. In some embodiments, the interchangeable head 64 includes at least one metal coagulation electrode 154 disposed at least partially over the position-tracking transducer 82 (FIG. 5), which electrically isolates the metal coagulation electrode(s) 154 from the elongated shaft 74. In some embodiments, as shown in FIG. 9A, the metal coagulation electrode(s) 154 is a single metal ring wrapped around the elongated shaft 74. In other embodiments, as shown in FIG. 9B, the metal coagulation electrode(s) 154 include two metal coagulation electrodes, for example, two metal rings (coaxially) wrapped around the elongated shaft 74. In some embodiments, the metal coagulation electrode(s) 154 provide electromagnetic shielding, discussed in the overview above. In some embodiments, the metal coagulation electrode(s) 154 covers at least 90% of an outward facing surface area of the position-tracking transducer 82. FIGS. 9A and 9B also show connections 156 for connecting the metal coagulation electrode(s) 154 with the console 50 (FIG. 1). The connections 156 may be covered by a plastic biocompatible sheath during use. The sheath generally does not cover the metal coagulation electrode 154. In some embodiments, the sheath may partially cover the metal coagulation electrode 154. The connections 156 extending from the metal coagulation electrode(s) 154 are secured, for example using self-adhesive tape 75, to the elongated shaft 74.

It should be noted that the disclosure described herein with reference to FIGS. 9A-11 may be implemented even when the medical instrument 28 does not include interchangeable heads or even if the head is deflectable.

Reference is now made to FIG. 10, which is a block diagram view of part of the console 50 of the medical procedure system 20 of FIG. 1 in accordance with an alternative embodiment of the present invention. The console 50 also includes a signal generator 158 in addition to the processing circuitry 38. The signal generator 158 is coupled to apply an electrical current to the metal coagulation electrode(s) 154 of FIG. 9A or 9B. The electrical current is typically a direct current (DC) or close to DC (i.e., a low frequency alternating current (AC) such as up to 20 KHz, by way of example only) as discussed in more detail above in the overview section.

Reference is now made to FIG. 11, which is a flowchart 160 including exemplary steps in a coagulation method performed by the medical procedure system 20 of FIG. 1.

The processing circuitry 38 is configured to receive (block 162) user input, for example via the operating controls 51, to commence a cutting action of the medical instrument 28. The processing circuitry 38 is configured to actuate (block 164) a cutting action of the cutting element(s) 78 (FIG. 5). In some embodiments, the cutting action may be initiated by pressing a switch (not shown) on the handle 62. The processing circuitry 38 is configured to control (block 166) the signal generator 158 to apply the electrical current to the metal coagulation electrode(s) 154 responsively to actuation of the cutting action by the cutting element(s) 78. In some embodiments, the processing circuitry 38 is configured to control (block 168) the signal generator 158 to maintain the electrical current applied to the metal coagulation electrode(s) 154 for a time period (e.g., up to 3 seconds, or more than 3 seconds) after ceasing the cutting action.

When the metal coagulation electrodes 154 comprise two metal coagulation electrodes, the signal generator 158 is coupled to apply the electrical current between the two metal coagulation electrodes 154. In some embodiments, the signal generator 158 is coupled to apply the electrical current between the metal coagulation electrode(s) 154 and the cutting element(s) 78 (FIG. 5). In other embodiments, the signal generator 158 is coupled to apply the electrical current between the metal coagulation electrode(s) 154 and at least one head surface electrode. In some embodiments, the position-tracking transducer 36 may comprise a head surface electrode.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A medical instrument including:
   (a) an elongated shaft having a distal end;
   (b) at least one cutting element disposed at the distal end of the shaft;
   (c) a position-tracking transducer disposed at the distal end of the shaft, and electrically insulated from the shaft and the at least one cutting element; and
   (d) at least one metal coagulation electrode disposed at least partially over the position-tracking transducer, wherein the position-tracking transducer is positioned and configured to electrically isolate the at least one metal coagulation electrode from the shaft.

2. The medical instrument according to claim 1, wherein the at least one metal coagulation electrode includes a metal ring wrapped around the shaft.

3. The medical instrument according to claim 1, wherein the at least one metal coagulation electrode covers at least 90% of an outward facing surface area of the position-tracking transducer.

4. The medical instrument according to claim 1, wherein the at least one metal coagulation electrode comprises a first metal coagulation electrode and a second metal coagulation electrode.

5. The medical instrument according to claim 4, wherein the first and second metal coagulation electrodes are coaxial with each other.

6. The medical instrument according to claim 1, wherein the at least one metal coagulation electrode is configured to electromagnetically shield the position-tracking transducer.

7. The medical instrument according to claim 1, wherein the at least one cutting element includes a shaving bur.

8. The medical instrument according to claim 1, wherein the at least one cutting element includes a shaving blade configured to rotate within the shaft.

9. The medical instrument according to claim 1, wherein the position-tracking transducer comprises a head surface electrode.

10. The medical instrument according to claim 1, wherein the position-tracking transducer includes at least one coil.

11. The medical instrument according to claim 10, wherein the at least one coil is printed on a circuit board, the at least one coil being coated with an electrically insulating material.

12. A medical system, comprising:
(a) the medical instrument according to claim 10, wherein the medical instrument is configured for inserting into a body part of a living subject; and
(b) a location pad having at least one magnetic field radiator configured to transmit alternating magnetic fields into a region where the body-part is located, the at least one coil of the position-tracking transducer being configured to detect at least part of the transmitted alternating magnetic fields.

13. A medical system, comprising:
(a) the medical instrument according to claim 1; and
(b) a signal generator coupled to apply an electrical current to the at least one metal coagulation electrode.

14. A medical system, comprising:
(a) the medical instrument according to claim 1; and
(b) processing circuitry configured to:
(i) receive signals generated by the position-tracking transducer, and
(ii) track a location of the distal end responsively to the received signals.

15. The system according to claim 14, wherein the medical instrument is configured for inserting into a body part of a living subject, the system further comprising a display, the processing circuitry being configured to render to the display an image including a representation of at least part of the body part and a representation of at least part of the medical instrument inserted in the body part responsively to the tracked location.

16. A medical instrument including:
(a) an elongated shaft having a distal end;
(b) an end effector disposed at the distal end of the shaft;
(c) a position-tracking transducer disposed at the distal end of the shaft, and electrically insulated from the shaft; and
(d) at least one electrode disposed at least partially over the position-tracking transducer, wherein the position-tracking transducer is positioned and configured to electrically isolate the at least one electrode from the shaft.

17. The medical instrument according to claim 16, wherein the end effector includes a cutting element.

18. The medical instrument according to claim 16, wherein the at least one electrode includes at least one metal electrode.

19. A medical instrument including:
(a) an elongated shaft having a distal end;
(b) an end effector disposed at the distal end of the shaft;
(c) a position-tracking transducer disposed at the distal end of the shaft, and electrically insulated from the shaft; and
(d) at least one electrode disposed at least partially over the position-tracking transducer, wherein the position-tracking transducer is positioned between the at least one electrode and the shaft.

20. The medical instrument according to claim 19, wherein the position-tracking transducer is positioned and configured to electrically isolate the at least one electrode from the shaft.

* * * * *